United States Patent [19]
Newell

[11] Patent Number: 5,121,107
[45] Date of Patent: Jun. 9, 1992

[54] INTRAVENOUS SUPPLY ALARM ASSEMBLY

[76] Inventor: John Newell, 29904 Downes Rd. R.R. #2, Mount Lehman, Canada

[21] Appl. No.: 558,052

[22] Filed: Jul. 25, 1990

[51] Int. Cl.⁵ .............................................. G08B 21/00
[52] U.S. Cl. ........................... 340/618; 128/DIG. 13; 340/612
[58] Field of Search ....................... 340/613, 618, 612; 128/DIG. 13; 200/85 R

[56] References Cited

U.S. PATENT DOCUMENTS

| | | | |
|---|---|---|---|
| 2,706,755 | 4/1955 | Krasno | 200/85 R |
| 3,287,721 | 11/1966 | Baehr | 340/613 |
| 3,389,387 | 6/1968 | Hulse et al. | 340/613 |
| 3,390,238 | 6/1968 | O'Neill | 200/85 |
| 3,992,706 | 11/1976 | Tunney et al. | 128/DIG. 13 X |
| 4,137,915 | 2/1979 | Kamen | 128/214 |
| 4,176,349 | 11/1979 | Fliegel | 340/613 |
| 4,224,610 | 9/1980 | Quinby | 340/614 |
| 4,378,014 | 3/1983 | Elkow | 128/214 |
| 4,598,733 | 7/1986 | Kanno | 137/406 |

Primary Examiner—Jin F. Ng
Assistant Examiner—Jeffery A. Hofsass
Attorney, Agent, or Firm—Seed and Berry

[57] ABSTRACT

An intravenous supply alarm assembly comprises a bladder adapted to contain an intravenous fluid, a support extending from the bladder and an alarm intimately associated with both the bladder and the support, said alarm operating to provide a signal when the volume of the intravenous fluid in the bladder is less than a predefined minimum.

18 Claims, 2 Drawing Sheets

INTRAVENOUS SUPPLY ALARM ASSEMBLY

BACKGROUND OF THE INVENTION

The present invention relates to the field of intravenous supply alarm systems.

Intravenous supply systems are widely used in medical treatments to supply nutrients, drugs, blood or blood products, etc. to patients. While intravenous (IV) supply systems have been used for many years, several improvements have been made to increase the safety and utility of the systems. The most notable improvement has been the disposable IV supply system.

Disposable IV systems are commonly fabricated from a clear thermoplastic material which is formed into a bladder or bag. The appropriate tubing and needle are integrally attached and the bladder is pre-filled with sterile intravenous fluids and is thus self-contained, requiring no extra equipment when used.

The plastic material and construction techniques employed allow the disposable IV supply systems to be fabricated at a minimal cost. They are thus immediately ready to use, when needed and may be conveniently discarded after use, removing any possibility of contamination of the supply or infection of a patient through reuse.

However, a problem exists with IV supply systems in general in that when the IV supply is exhausted, there is a possibility that an air bubble may be allowed to enter the patient's vein through the feed tubing. This air bubble may lead to the formation of an air embolism with serious consequences to the patient.

Thus, it is necessary for medical personnel, or the patient, to closely monitor the level of fluid in the supply at all times. Placing this responsibility on the patient leads to increased anxiety and general discontent with the use of the IV supply systems. There have been several prior attempts to overcome the problem of monitoring the supply level in IV systems.

U.S. Pat. No. 2,706,755 to Krasno shows an alarm device from which an intravenous supply bottle is hung. The device has a moveable plate which is biased by a spring against two electrical contacts to complete an electric alarm circuit. The supply bottle is suspended from a hook attached to the plate and the weight o the bottle and its contents act against the spring to move the plate away from the electrical contacts, opening the circuit. As the contents of the supply bottle are fed into the patient, the weight acting against the spring is reduced and the plate moves towards the electrical contacts. When the supply is almost fully displaced from the bottle, the weight is reduced to the point that the plate completes the circuit and activates the alarm.

U.S. Pat. No. 3,389,387 to Hulse et al. shows a similar alarm device which monitors changes in the weight of the supply container due to changes in the amount of supply fluid. As the container empties, a spring biased member is moved from a position in contact with a circuit-opening switch to a position out of contact with this switch thus closing the circuit and signalling a medical attendant.

U.S Pat. No. 3,390,238 to O'Neill shows a fairly complex alarm device which is adjustable to accommodate supply assemblies of different weights, due to differing amounts of supply fluid and/or different densities of various supply fluids.

These prior alarm devices all suffer from numerous disadvantages in practise. Firstly, they are bulky units, separate from the IV containers, which must be set up in association with the IV containers prior to use. In current medical practice, however, it is desirable that all treatments and apparatus be self-contained whenever possible. Secondly, they must be re-used and transferred from one IV container to the next thus increasing the likelihood of breakage. Thirdly, repeated use of these units necessitates repairs and performance monitoring. Fourthly, these units are expensive to manufacture with numerous and detailed component parts. Due to the aforementioned problems, these devices have not attracted significant commercial interest.

SUMMARY OF THE INVENTION

It is an object of the present invention to obviate or mitigate the above disadvantages.

The present invention provides an intravenous supply assembly comprising a bladder adapted to contain an intravenous fluid, a support means extending from the bladder and an alarm means associated with both the bladder and the support means, said alarm means operating to provide a signal when the volume of the intravenous fluid in the bladder is less than pre-defined minimum.

In a preferred form, the alarm means comprises spaced contacts, an upper contact associated with the support means and a lower contact associated with the bladder, said spaced contacts being movable into electrical engagement when the volume of the bladder reaches a level at which it is deemed appropriate to notify medical personnel so as either to disconnect the intravenous supply assembly from the patient or to replace the used bladder with a new bladder. In a very preferred form, the alarm means is secured to and more preferably partially or fully integral with the bladder and the support means.

The intravenous supply assembly of the present invention is a simple and effective warning system for patients and medical personnel alike. The use of the alarm means as described herein significantly reduces the chance of an unchecked, empty intravenous bladder passing air into the vein of a patient to which it is attached. The alarm means is designed to comprise a minimal number of parts so that in the preferred form, it can be manufactured, sold and ultimately discarded with the intravenous bladder and support means.

BRIEF DESCRIPTION OF THE DRAWINGS

A preferred embodiment of the present invention will now be discussed, by way of example only, with reference to the following figures wherein:

In FIG. 1, an intravenous supply assembly is indicated generally at 10. The supply assembly consists of a bladder or bag 12 containing the intravenous fluid 14, tubing 16 for attachment to the intravenous catheter, not shown, and support arms 18, 18' from which the supply is suspended.

DESCRIPTION OF THE PREFERRED EMBODIMENTS

Figure 1:
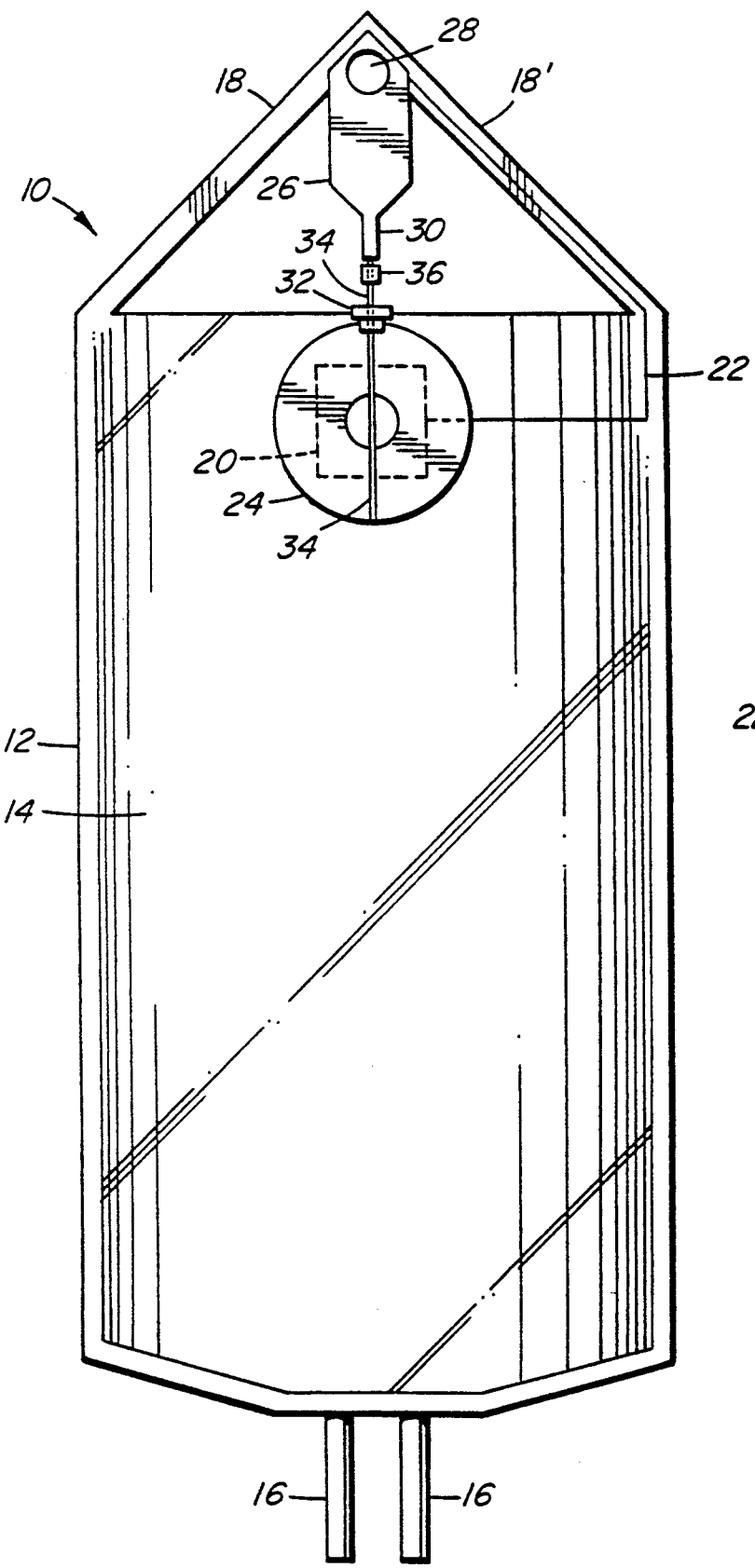
FIG. 1 shows an intravenous supply assembly.

A battery 20 is preferably wafer-shaped with each side of the wafer being one terminal of the battery. One terminal, the positive for example, has an insulated conductor 22 electrically connected to it and is bonded to one side of the bag 12, near its top, between the points where the support arms 18, 18' connect to the bag 12. Thus the positive terminal of the battery, in this case, abuts the bag 12.

A buzzer or beeper 24, preferably of the piezoelectric type, is bonded to the battery 20 in such a fashion that one electrical terminal of the buzzer 24 is in electrical contact with the other terminal of the battery, in this case the negative terminal.

The conductor 22 is arranged to connect to a flange 26 located at the vertex formed by the support arms 18, 18'. Preferably, the flange is of metal.

The metal flange 26 is attached to the support arms 18, 18' to which the conductor 22 is electrically connected. The flange 26 has a hole 28 at its upper extremity through which, when the supply assembly is in use, a support hook may be placed. Thus the weight of the supply assembly 10 is borne, through the flange 26, by the support arms 18, 18'.

The metal flange 26 has a metal tab 30 depending from its lower edge towards the buzzer 24. This tab serves as the upper conductor. A ring-shaped electrical connector 32 is attached to the buzzer 24 with its center opening orientated towards the tab 30. The ring-shaped connector 32 serves as the lower conductor and is electrically connected to the second of the buzzer's electrical terminals.

A length of resilient material 34, passes through the center of the ring-shaped connector 32 and has one end attached to tab 30 and the other end attached to the lower edge of buzzer 24.

In a preferred embodiment, bag 12 and support arms 18, 18' are integrally formed of a clear or translucent, thermoplastic material. Alternatively, however, the support arms may not be integral with the bladder and may be of string, cloth or resilient material such as elastic or rubber.

In a preferred embodiment, conductor 22 is attached to the outside of bag 12 for a portion of its length and is embedded into one support arm, for example 18', for the remainder of its length. In another embodiment, conductor 22 is integrally formed in bag 12 and support arm 18' along its entire length. Accordingly, the conductor is protected from possible damage during transport and use.

Preferably, the resilient material is elastic, most preferably a durable elastic band. The length, size and resiliency factor of the resilient material are selected to ensure that, when the intravenous fluid in the bag or bladder reaches a pre-defined level of emptiness, the stretched, resilient material will retract and cause the upper contact (tab 30) and lower contact (connector 32) to join in electrical association. Thus, the resilient material may not be excessively taut so as not to permit retraction when required but at the same time it must be sensitive enough to detect the reduction in volume of intravenous fluid in the bag. Given the simplicity of the assembly, it would be a straightforward matter to select an appropriate resilient material and an appropriate size for this material to ensure that the alarm is not activated until the pre-defined level of emptiness is reached.

Generally, the densities of various intravenous fluids, whether the fluid is blood or saline etc... are generally equivalent as the major portion of these fluids is water. However, in some instances, it may be necessary to adapt the length and/or size of the resilient material based on different densities of the intravenous fluid in the bladder. Adjustments to the resilient material can be readily made by one skilled in the art.

In operation, the intravenous supply assembly of the present invention is placed on a support hook through hole 28. The weight of the assembly 10 including fluid 14 and bladder or bag 12 is supported by the support arms 18, 18'. When more than a pre-defined minimum volume of fluid is present in the bladder, the combined weight of the assembly is greater than the bias force of resilient material 34 and accordingly, the upper conductor (tab 30) and the lower conductor (connector 32) are spaced apart, the circuit is open and thus the alarm is not activated. The resilient material is in an extended state. The intravenous bag is connected to the patient by way of the intravenous catheter and intravenous feeding is initiated. The volume of fluid 14 in bladder 12 thus decreases as it is fed into the patient.

Figure 2:
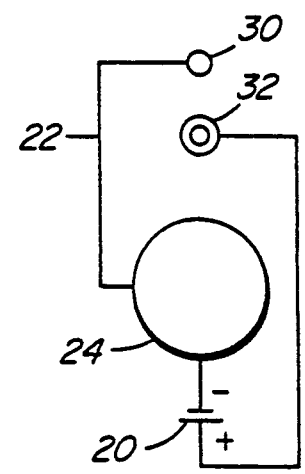
FIG. 2 shows a schematic of an electrical circuit for the assembly shown in FIG. 1.

When the volume of intravenous fluid reaches a pre-defined minimum, which can be any level of fluid depending on the individual application and the pre-assessed strength of the resilient material, the resilient material, at one end secured to the lower conductor and the bladder, retracts thus moving the upper conductor and the lower conductor into physical contact. This physical contact closes the circuit between buzzer or beeper 24, battery 20, the upper contact (tab 30) and the lower contact (connector 32), thus activating the alarm. The arrangement of this circuit is depicted in FIG. 2. Once the alarm is activated, the patient may be provided with a new intravenous supply assembly, or may be disconnected from the assembly.

To avoid the possibility of accidental activation of the alarm when shipping or storing the intravenous supply assembly, an insulating means such as an insulating grommet 36 may be placed between the upper conductor and the lower conductor. Preferably, the grommet is removably secured to resilient material 34. Most preferably the grommet is permanently attached to the assembly, i.e. by way of a thread attachable to one of the support arms. This way, the grommet may be readily replaced between the upper conductor and the lower conductor after the alarm is activated, in order to stop the alarm. Prior to use, this grommet may be removed and the bag lifted to allow the upper conductor (tab 30) and the lower conductor (connector 32) to contact and sound the alarm. In this manner, the operation of the alarm may be verified.

The volume remaining in the bag at the point of activation of the alarm includes a wide range of volumes. Ideally, whatever "trigger" volume is chosen, it should allow medical personnel enough time to take the appropriate action, i.e. discontinue the flow of IV fluid, change the IV supply bladder, remove the entire assembly by disconnecting it from the patient, etc.... Of considerable importance in deciding what the pre-defined minimum volume should be is the reservoir under an IV supply assembly which holds as a safety measure, after depletion of the bladder, approximately 10 cc. of fluid. In addition, the IV catheter holds an additional small safety reservoir. Taking these factors into consideration, it is preferred that the pre-defined minimum volume of fluid be between 5–25 cc., more preferably between 10–20 cc.

Figure 3:
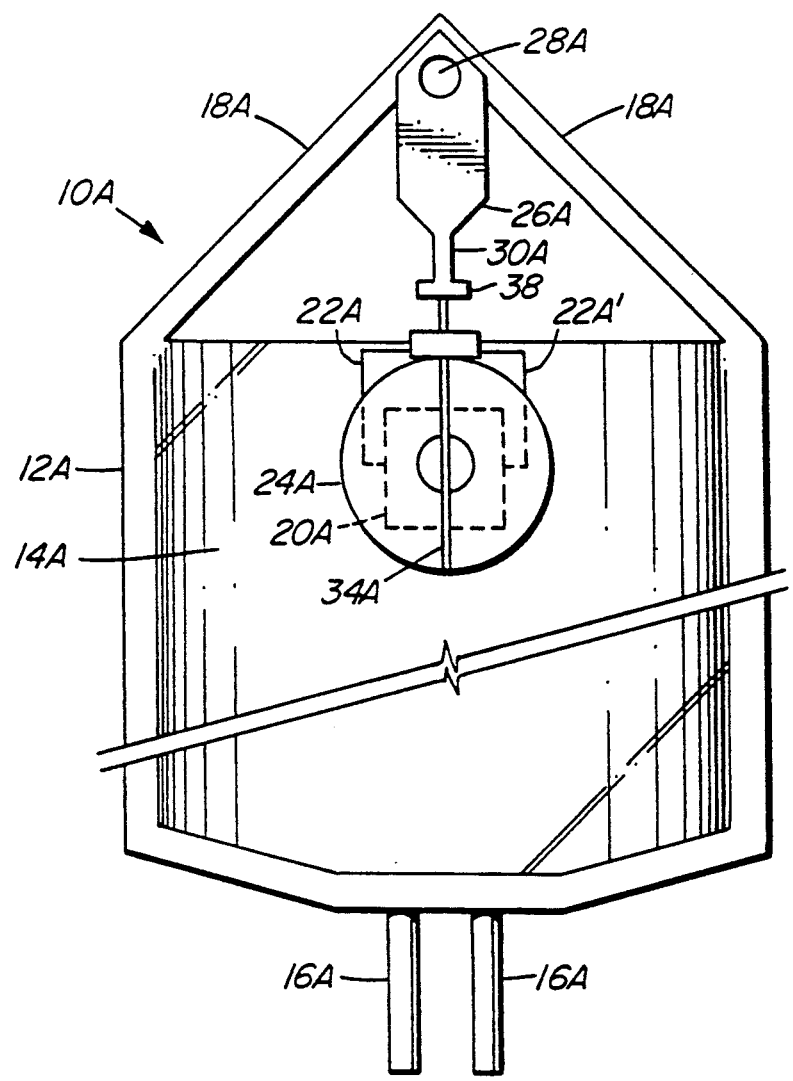
FIG. 3 shows another embodiment of an intravenous supply assembly.
Figure 4:
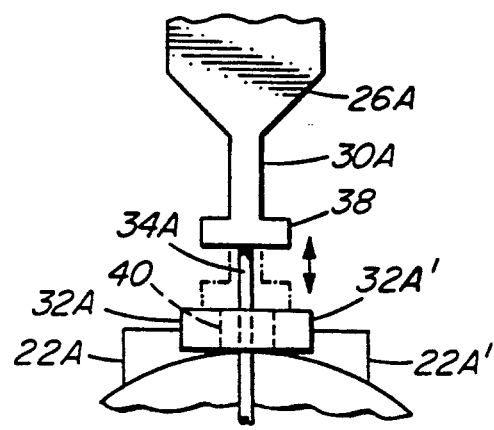
FIG. 4 shows the engaged contacts of the assembly of FIG. 3.

In another embodiment of the invention shown in FIGS. 3 and 4, wherein similar components for clarity are identified with an appended subscript "A", the electrical contacts $32_A$ and $32_A$, are connected to electrical conductors $22_A$ and $22_A$ respectively. Conductor $22_A$ is in electrical contact with a terminal of the batter $20_A$ and conductor $22_A$, is in electrical contact with a terminal of the buzzer $24_A$. As in the previous embodiment, the other terminal of the buzzer $24_A$ and the battery $20_A$ are also in electrical contact. In this embodiment, tab $30_A$ has a foot 38 which is wide enough to touch both contact $32_A$ and $32_A$, simultaneously.

The two contacts $32_A$ and $32_A$, are separated by an insulating material 40 to open the electrical circuit of the alarm. The contacts are bonded to the top of the bag, below the foot 38. In use, as the fluid level in the bag drops to the predefined minimum level, the resilient material 34A moves the foot 38 into electrical engagement with the two contacts $22_A$ and $22_A$, thus completing the circuit and sounding the alarm.

It should be understood that other embodiments are envisaged, including those utilizing other contact arrangements or micro-switches. These other embodiments will be apparent to those skilled in the art.

It should be understood that the alarm of the present invention need not be auditory. It will be apparent to those of skill in the art that a light source, such as a light emitting diode, may be favorably employed in place of, or in conjunction with the above-mentioned buzzer and other types of alarm may be apparent to those of skill in the art.

Due to the simplicity of the design of the alarm means, it is preferred that the alarm is partially or fully integral with the bladder and support means. This way, the entire assembly is set up without the need, as a separate step, to attach an alarm to the bladder and support means. The manufacture of an assembly comprising a bladder, a support means and an alarm means would not be significantly higher in terms of costs than a conventional bladder alone due to the ready availability and simplicity of the component parts. In any event, the benefit in safety and convenience of an alarm secured to each intravenous bladder far outweighs the minimal cost increase.

It should thus be understood that the present invention is not limited to the above embodiments, and that other uses and forms within the scope of the invention may be envisaged by those of skill in the art.

We claim:

1. An intravenous alarm assembly comprising:
a flexible reservoir adapted to contain intravenous fluid;
support means, extending from the reservoir for supporting the assembly;
alarm means connected between said reservoir and support means, having a first electrical contact connected directly to said reservoir and a second electrical contact associated with the first contact; and
means to establish an electrical connection between said first and said electrical contacts when the volume of the intravenous fluid in the reservoir is less than said predefined minimum volume, said alarm means providing a signal in response to said electrical connection.

2. The intravenous alarm assembly of claim 22 wherein:
said second electrical contact is connected to the support means; and
said means to establish a connection between said first and second electrical contact is a biasing member for biasing said electrical contacts together, said electrical contacts moving into electrical engagement when the volume of the intravenous fluid in the reservoir is less than said pre-defined minimum volume, thereby operating said alarm means.

3. The intravenous alarm assembly of claim 22 wherein:
said second electrical contact is connected directly to said reservoir and spaced from said first electrical contact;
said means to establish an electrical connection between said first and second electrical contacts is a circuit-completing means, connected to the support means; and
further including a biasing means acting between said electrical contacts and the circuit-completing means to urge said electrical contacts into contact with said circuit completing means when the volume of intravenous fluid in the reservoir is less than said pre-defined minimum volume, thereby operating said alarm means to provide said signal.

4. The intravenous alarm assembly of one of claim 2 or 3 wherein said alarm means produces a visual alarm.

5. The intravenous alarm assembly of one of claim 2 or 3 wherein said alarm means produces an audible alarm.

6. The intravenous alarm assembly of claim 22 wherein said support means is flexible.

7. The intravenous alarm assembly of claim 1 wherein said biasing means is an elastic member extending between said support means and said reservoir.

8. The intravenous alarm assembly of claim 3 wherein said biasing means is an elastic member extending between said circuit-completing means and said reservoir.

9. The intravenous alarm assembly of claim 8 wherein said spaced electrical contacts are separated from one another by an insulating spacer member.

10. The intravenous alarm assembly of claim 1 wherein said support means is a pair of converging, inclined arms extending upwardly from said reservoir and terminating at an apex, said upper electrical contact extending downwardly from said apex.

11. An intravenous alarm assembly comprising:
a reservoir adapted to contain intravenous fluid;
supports means, extending from the reservoir, for supporting the assembly;
alarm means including an upper electrical contact connected to said support means, and a lower electrical contact directly connected to the reservoir, said alarm means for indicating when the volume if intravenous fluid is below a pre-defined minimum volume;
signalling means, electrically connected between both the upper electrical contact and the lower electrical contact, for initiating the alarm means; and
biasing means for biasing said electrical contacts into electrical engagement when the volume of intravenous fluid in the reservoir is less than the predefined minimum volume.

12. The intravenous alarm assembly of claim 11 wherein said alarm means produces a visual alarm.

13. The intravenous alarm assembly of claim 11 wherein said alarm means produces an audible alarm.

14. The intravenous alarm assembly of claim 11 wherein said support means is integrally formed with said reservoir.

15. The intravenous alarm assembly of claim 13 wherein said signalling means comprises a beeper.

16. The intravenous alarm assembly of claim 11 wherein said biasing means is an elastic member.

17. The intravenous alarm assembly of claim 11 wherein the reservoir is a flexible bladder.

18. The intravenous alarm assembly of claim 17 wherein said support means is a pair of converging, inclined arms extending upwardly from said reservoir and terminating at an apex, said upper electrical contact extending downwardly from said apex.

* * * * *